US006962496B2

(12) United States Patent
Houri et al.

(10) Patent No.: US 6,962,496 B2
(45) Date of Patent: Nov. 8, 2005

(54) RECOGNITION OF SCENTS IN FRAGRANCES

(75) Inventors: Jean-Pierre Graziano Houri, Folkestone (GB); Shibani Mohindra, Orpington (GB); Phillipe Durand, Hythe (GB); Isabelle Pupier Stefanesco, Madison, NJ (US)

(73) Assignee: Quest International Servces B.V., Naarden (NL)

( * ) Notice: Subject to any disclaimer, the term of this patent is extended or adjusted under 35 U.S.C. 154(b) by 0 days.

(21) Appl. No.: 10/480,592

(22) PCT Filed: Jun. 14, 2002

(86) PCT No.: PCT/GB02/02700
§ 371 (c)(1),
(2), (4) Date: Dec. 12, 2003

(87) PCT Pub. No.: WO02/102433
PCT Pub. Date: Dec. 27, 2002

(65) Prior Publication Data
US 2004/0191750 A1 Sep. 30, 2004

(30) Foreign Application Priority Data
Jun. 16, 2001 (GB) .............................................. 0114807

(51) Int. Cl.⁷ .............................................. G09B 25/00
(52) U.S. Cl. ..................................................... 434/365
(58) Field of Search ................... 434/365, 81; 206/232, 206/570, 308.1

(56) References Cited
U.S. PATENT DOCUMENTS

| | | | |
|---|---|---|---|
| 4,012,720 A | * | 3/1977 | Call et al. .................... 235/443 |
| 4,446,671 A | * | 5/1984 | Stalder ......................... 53/445 |
| 5,041,972 A | * | 8/1991 | Frost ............................ 705/10 |
| 5,217,378 A | * | 6/1993 | Donovan ..................... 434/116 |
| 5,591,409 A | | 1/1997 | Watkins |
| 5,724,256 A | | 3/1998 | Lee et al. |
| 5,913,204 A | * | 6/1999 | Kelly .......................... 705/500 |
| 6,169,595 B1 | | 1/2001 | Manne |
| 6,223,912 B1 | * | 5/2001 | Nerushai et al. ........... 211/59.2 |

FOREIGN PATENT DOCUMENTS

| | | | |
|---|---|---|---|
| WO | WO 99 01793 A | 1/1999 | |
| WO | WO 00 58172 A | 10/2000 | |
| WO | WO 0209776 | * 7/2004 | ............. A61L/9/00 |

* cited by examiner

Primary Examiner—Chanda L. Harris
(74) Attorney, Agent, or Firm—Morgan, Lewis & Bockius LLP

(57) ABSTRACT

Educational/diversionary apparatus is arranged to present a user with various different scents and data thereon in order to aid scent recognition and enable a user to decide upon a combination of scent types which would be desirable to him/her. The apparatus takes the forms of a kit having a number of different scents and data carrying means, such as a CD Rom, which holds data on the nature, geographical origin and/or source of each of the said scents, wherein the data held on the data carrying means includes a map showing a number of geographical regions and cross-referencing means for cross-referencing each region with an associated scent. The selection of a region by the user can thus result in an associated scent being identified and data on that scent being presented to the user. The data on the carrier preferably comprises a computer program having instructions for causing a computer to display an image of the map and to provide means for selecting an area on the map. The apparatus may also be arranged to cause the computer to accept inputs from the user representative of the relative desirabilities of scents in the kit, and means for generating a display representative of said desirabilities.

10 Claims, 27 Drawing Sheets

PART 2

This part is about virtual travel around the world. The objective is to learn the 14 lignes de force and to smell characteristic ingredients in each of the families.

There are 3 levels:

-Level 1 "cultural", the complete package!

-Level 2 "connoisseur" if you already know the 14 families

-Level 3 "mood-oriented", more fun, for 2nd time users

Level 1 "cultural" is the main option, the one you will necessarily take the first time you enter Perfume Voyage -You visit all the countries and smell all the ingredients from the kit -You experiment with the 5 senses with the explorations -You learn about the lignes de force -You rank the families by order of preference and based on that liking you design your customised ligne de force Level 2 "connoisseur", a pre-selected itinerary -First you pick up the family of your choice -You travel only to the countries related to this family -You only go to the places highlighted on the map Level 3 "mood-oriented", a pre-selected itinerary -First you select your mood, e.g. in love, energising, relaxing etc...

-Depending on how you feel, you'll go to pre-selected countries

-The selection refers to ingredients in harmony with your mood

Fig. 3H

The perfume voyage starts here
Our little perfumer asks the player to choose level 1, 2 or 3.

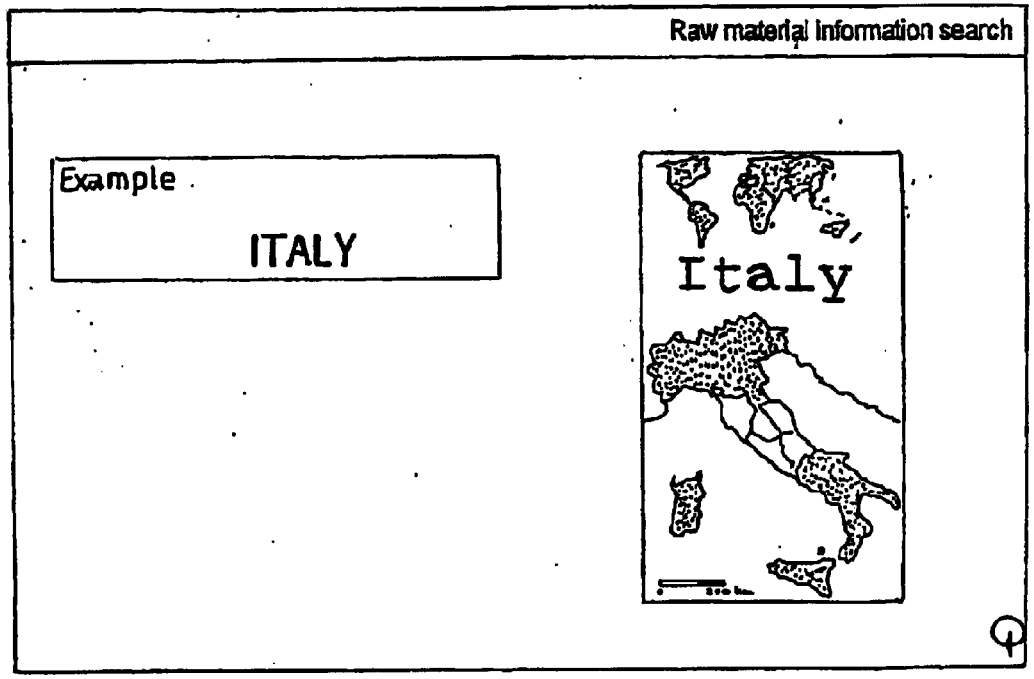
What's behind a country? Let's take the example of Italy  Fig.5A
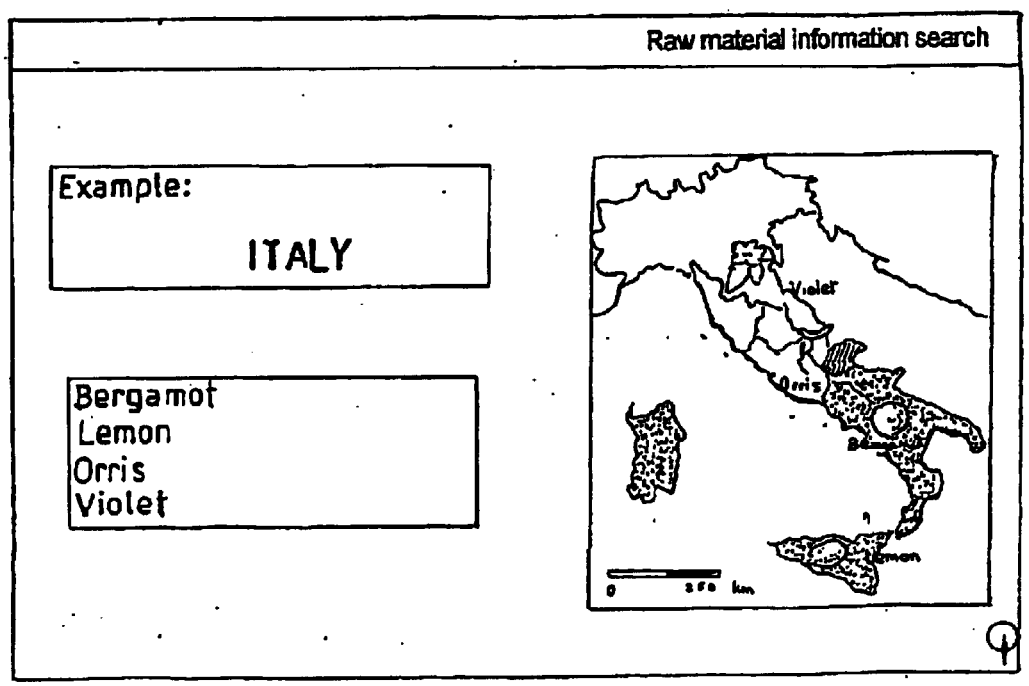
Fig.5B

Fig. 5C

Let's smell lemon!

Lemon – *citrus limmonum*

The oil, *Oleum Limonis*, is more valuable and odourous if it is obtained by expression, rather than distillation. The main form of isolating the oil is by squeezing the peel of the ripe fruit using special machines. Although, other methods have been employed, like that of the 'Essence de Citron distillee' whereby the fresh lemons are rubbed on a coarse tin grater, the grated peel then being distilled in water. The yield, which strongly depends on the production procedure can reach between 0.6 % - 0.8%. A 1000 lemons will yield something between 1-2 pounds of essential oil. The Immature fruit yielding less, and being of inferior quality.

The *Citrus Limonum*, of the N.O. Rutaceae family, also known as Citrus Medica., Citronnier, Neemoo, Leemoo, And Limone, is indigenous to Northern India, but is presently being widely cultivated in all of the Mediterranean countries along with Brazil, U.S.A., Argentina, Israel, and West Africa. The lemon is thought to have reached Europe by way of Persia or Media, being grown first in Greece, then Italy in the Second Century. Today there are more than 45 different varieties.

*Limonum* is derived from the Arabic of 'Limun', or 'Limu', which is thought to have come from the Sanskrit *Nimbuka*. Its medical virtues and benefits continue to such an extent that it has been stated by *Mrs. M. Grieve*, author of 'A Modern Herbal', "that the lemon is the most valuable of all fruit for preserving health."

INDIA/HERBAL FAMILY

-Indians believed that basil had been touched by their gods and had a divine essence. Because of this, they used it in the swearing of oaths and for other ceremonial and holy purposes.

-Basil → Herbal Family

-Smelling of basil and lavender

-Cooking Exploration → recipes with basil and lavender

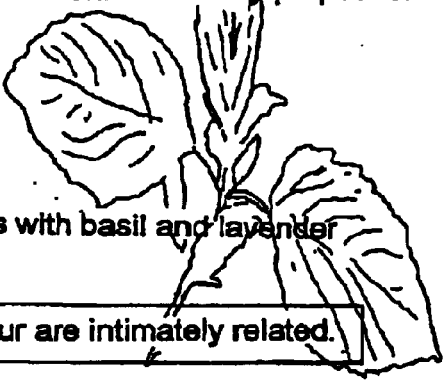

> ↳ Conclusion 4: Smell & Flavour are intimately related.

Fig. 8

EGYPT/GREEN FAMILY

The Roman naturalist and scientist Pliny claimed that galbanum was an ingredient of meloplan a famous Egyptian perfume, but no traces of the resin have ever been found in Egyptian tombs.

-Galbanum → Green Family

-Smelling of galbanum and hyacinth

-"Visual" Exploration → Association with green landscapes

Display of different types of landscape (Amazon forest, fields, mountain in summer etc...)

> ↳ Conclusion 5: Fragrance and spirituality

Fig. 9

USA / FLORAL FAMILY

USA(anecdote about jazz singer Billie Holiday who used to wear a gardenia flower in her hair during her concerts)

- Gardenia →Floral Family
- Smelling of gardenia, rose and mimosa
- "Musical" Exploration →Association with music Pre-selection of music from different cultures and times Which music will best suit this smell ?

> Conclusion 8: "Like music, fragrances are about harmony and rhythm" (P.Durand)

Fig. 12

FRANCE / LEATHER FAMILY

-Grasse- Smells of leather and fine fragrance have been intermingled for centuries. One of the main centers for creating perfume was initially the center of leather processing industry. In the 16th century, no method had been invented for cleaning leather. Leather was therefore heavily perfumed.

-Smelling

-Exploration: Blind smelling of genuine/non genuine leather. (Leather provided in kit)

> Conclusion 9: Smell influence our other senses

Fig. 13

The 4 last families (leather, marine /ozone, fruit, sweet & powdery) will have in common a multi-sensorial exploration.
By picking colors, fabrics...set a scene which will suit each family.

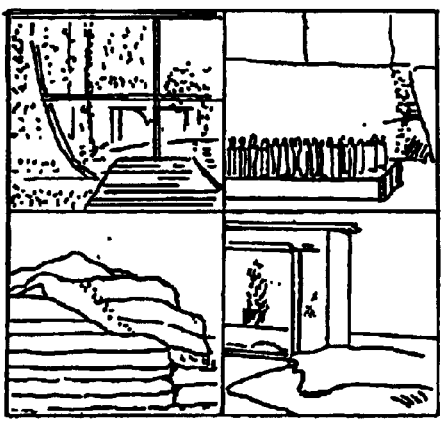

Fig.18

UNDERSTANDING AND SPEAKING THE LANGUAGE OF PERFUMERY

-Recap of all the previous conclusions

-MCQ with scoring

-Smell is the most intimate of the senses. It is also the most difficult to describe How do you tell someone about a particular fragrance ?

Is there a way to describe fragrances ?

Introducing here the lignes de force (See exploratorium)

Fig.19

CHECK LIST

What the user has been doing so far?

- ☒ Learning in general
- ☒ Learning about perfumery
- ☐ Learning about fine fragrances
- ☒ Smelling
- ☐ Creating
- ☒ Interacting
- ☐ Communicating with Quest
- ☐ Communicating with other users
- ☒ Having fun This slide is just a check-list of the key points we had discussed when we started the project

Fig. 20

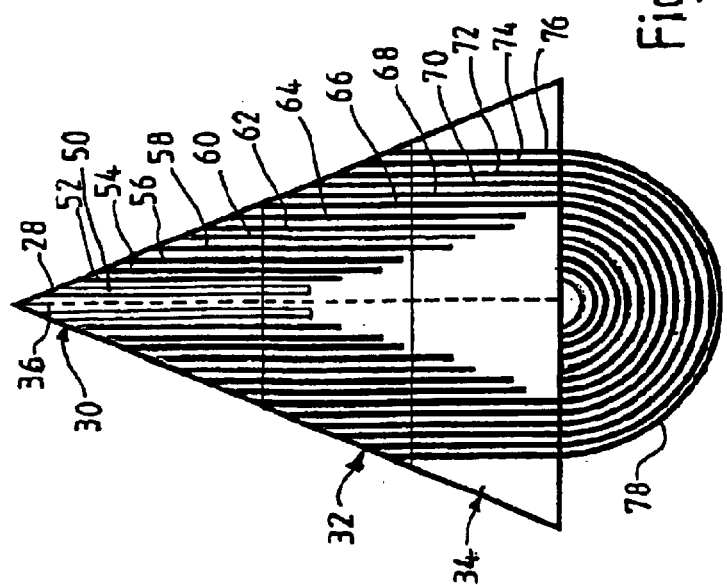

Fig. 22

When the triangle is transformed into a cone, a cross section would give a series of circles, each corresponding to a specific Ligne de Force

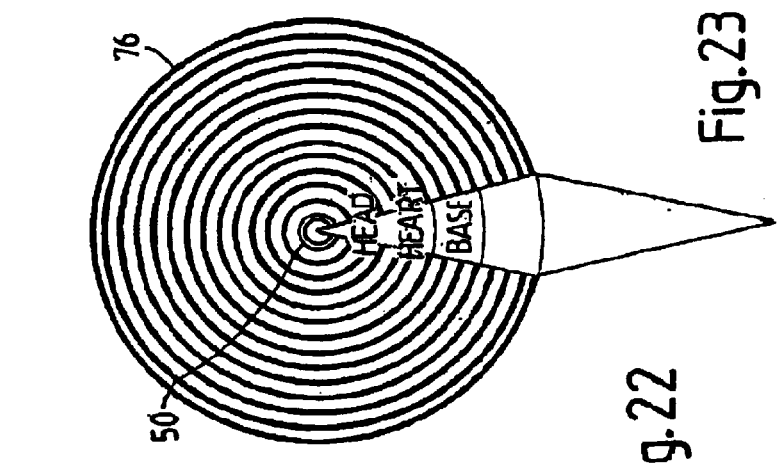

Fig. 23

The circles near the centre indicate HEAD notes followed by the HEART notes, with the BASE notes on the outer part of the diagram. The intensity of the Lignes de Force can be indicated by the width of each band

Fig. 24

The diagram shows the profile of CHANEL 5. The HEAD notes are dominated by an aldehydic accord supported by a touch of citrus. The HEART consists essentially of a floral and wood bouquet with a touch of spice. The soft BASE notes consist of vanilla and musk, made more sensual by a light animalic accord Odour profile of twelve leading masculine fragrances Odour profile of twelve leading feminine fragrances

| HOW TO SWITCH LOGICALLY FROM LIGNES DE FORCE TO PERFUME PLANETS ? |
|---|
| Smell again the Ingredients representatives of each ligne de force<br><br>Which ones do you like ? (Give a mark to each of them)<br><br>Which one do you prefer ? Why ?<br><br>Which ones would you spontaneously reject ?<br><br>(Answers entered and processed)<br>    ODOR PROFILE (i.e. a recap of the type of ingredients they like)<br>    LIGNE DE FORCE PROFILE (Using the marks)<br>    Following this profile, create your personal mini-accord by mixing your favourite ingredients from the kit |

Fig. 27

Example

Let's assume the user has selected plum, mandarin, violet and rose as his favourite ingredients.
His odor profile will be fruity floral

RECOGNITION OF SCENTS IN FRAGRANCES

FIELD OF THE INVENTION

This invention relates to educational apparatus for presenting a user with scents and information thereon. Such apparatus may additionally or alternatively provide a user with a profile indicative of the fragrance families which that person is likely to prefer. The invention is particularly applicable to the recognition of scents in perfumes for personal use.

BACKGROUND OF THE INVENTION

A wide range of different perfumes are used as ingredients for many commercially available products, especially toiletries. Where a perfume is dominated by a scent originating from any single, readily identifiable source (for example a citrus fruit such as lemon), many users can normally easily recognise the scent.

However, many perfumes comprise a complex blend of various different ingredients, some of which produce very subtle scents. Few people are able, without special training, to identify individual scents in such perfumes, and therefore find it difficult to associate perfumes with the varied and (sometimes) rather obscure descriptions often provided on the packaging of the perfumes. Consequently, many people tend to select a new perfume on a "trial and error" basis.

SUMMARY OF THE INVENTION

According to the invention, there is provided educational and/or diversionary apparatus for presenting a user with scents and data thereon, the apparatus comprising a kit containing a number of different scents and data carrying means which holds data on the nature, geographical origin and/or source of each of the scents, wherein data held on the data carrying means includes a map showing a number of geographical regions and cross referencing means for cross referencing each region with an associated scent, such that the selection of a region by the user results in the associated scent being identified.

It is believed that the referencing of each scent to a respective geographical region, and the provision of information on a scent in response to the selection of such a region enable a user more readily to remember, recognise and describe the scent and its characteristics.

Each scent may be associated with its region by virtue of any characteristic which is relevant to that region. Thus a scent may be associated with a particular country famous as a source for that scent, or in which that scent was first made, or with a region, such as an ocean, because the scent has similar characteristics of freshness to that of the ocean.

A scent may also be associated with a given country by virtue of having been popular in that country.

The data on the carrier may take the form of printed matter, but preferably comprises a computer program having instructions for causing a computer to display an image of the map and to provide means for selecting, using an input device on the computer, an area on the map, wherein the selection of any given region causes the computer to retrieve and display information on the associated scent.

The program is preferably also operable to cause a computer running the program to invite the user to sample a scent (by smelling it). In this case, the program is also preferably operable to cause such a computer to record data, which is entered by the user and which is indicative of his or her perception of the desirability of the sampled scent. The invitation may be given using an animation depicting a person or character asking the user to sample the scent.

The data may, for example, be a numerical score, the higher the score the more desirable the scent.

Preferably, the program, in use, causes a computer to prompt the user to enter said data and puts the computer in a condition to receive said data after having displayed instructions for the user to try the scent and having displayed information on the scent, and before allowing another region to be selected.

Preferably, the program includes instructions for causing a computer to create, from said inputs, an output representative of the relative desirabilities of the previously sampled scents.

The output may to advantage take the form of a graphical representation of relative desirabilities of sample scents.

It is known to categorise scents into different olfactive groups, each containing scents of similar characteristics (e.g. floral, spicy, herbal etc.). Preferably, the graphical representation comprises a series of coloured elements, each corresponding to a respective group containing a scent that has been sampled.

The elements may to advantage comprise concentric rings, the thickness of each of which is proportionate to the desirability of the respective scent in the group represented by that ring.

Such a representation corresponds to the Lignes de force developed by Quest International to provide a graphical representation of various known types of perfume. According to the Lignes de force scheme, the thickness of any given ring corresponds to the prominence of a given category of scent in a perfume. Thus, by comparing his or her own profile, as prepared by the computer, with the recorded Lignes de force representations of various known scents, a user can more readily find a perfume which is likely to appeal to him or her.

The invention therefore also lies in apparatus for providing an indication of the types of fragrances that a user is likely to prefer, the apparatus comprising a plurality of scents in different predetermined families, a data carrier on which, there is provided a computer programme for causing a computer to instruct a user to sample each scent in turn, and enter data representative of the desirability of each scent and to display a graphical representation of the relative desirabilities of the families (based on said inputs).

Preferably, the scents are in a liquid form, each scent being held in a respective container, and the apparatus includes substrate means for receiving a portion of scent to be smelt.

Preferably, the substrate means is absorbent, and conveniently comprises a number of pieces of sheet material, for example strips of paper. Alternatively, the substrate means may comprise non-paper absorbents, for example as supplied by Ilacon Ltd (Tunbridge, UK) under the name "scribrod inners type 7446", polymer matrices or inorganic matrices (for example silica or zeolites).

Preferably, the apparatus also includes a receptacle for mixing individual scents and dispensing means, for example droppers, or other delivery devices for transferring controlled amounts of scents from their containers to the receptacle.

Preferably, the apparatus also includes one or more materials, such as leather or a fabric, associated with a given scent.

BRIEF DESCRIPTION OF THE DRAWINGS

The invention will now be described, by way of example only, with reference to the accompanying drawings in which:

FIGS. 3A–3I show examples of the text and graphics displayed on a computer running a program on the CD Rom, said text and graphics providing an introduction to the use of the apparatus;

FIGS. 5A–5F, 6A–6C, 7A–7C, and 8–17 show examples of displays of information on said regions, scents and/or families of scents;

FIGS. 18–20 show further information which is displayed after the user has stopped selecting regions;

FIG. 22 is a diagram indicating the way in which scents can be represented in accordance with the applicant's Lignes de force system;

FIG. 23 is a neutral Ligne de force diagram (showing all scent components with equal prominence);

FIG. 24 is a corresponding diagram showing a profile of Chanel No. 5;

FIGS. 27–29 show further text and graphics which may be displayed by the computer and which relate to further categorisation of fragrances to help a user establish the types of fragrance which he/she is likely to prefer.

DESCRIPTION

Figure 2:
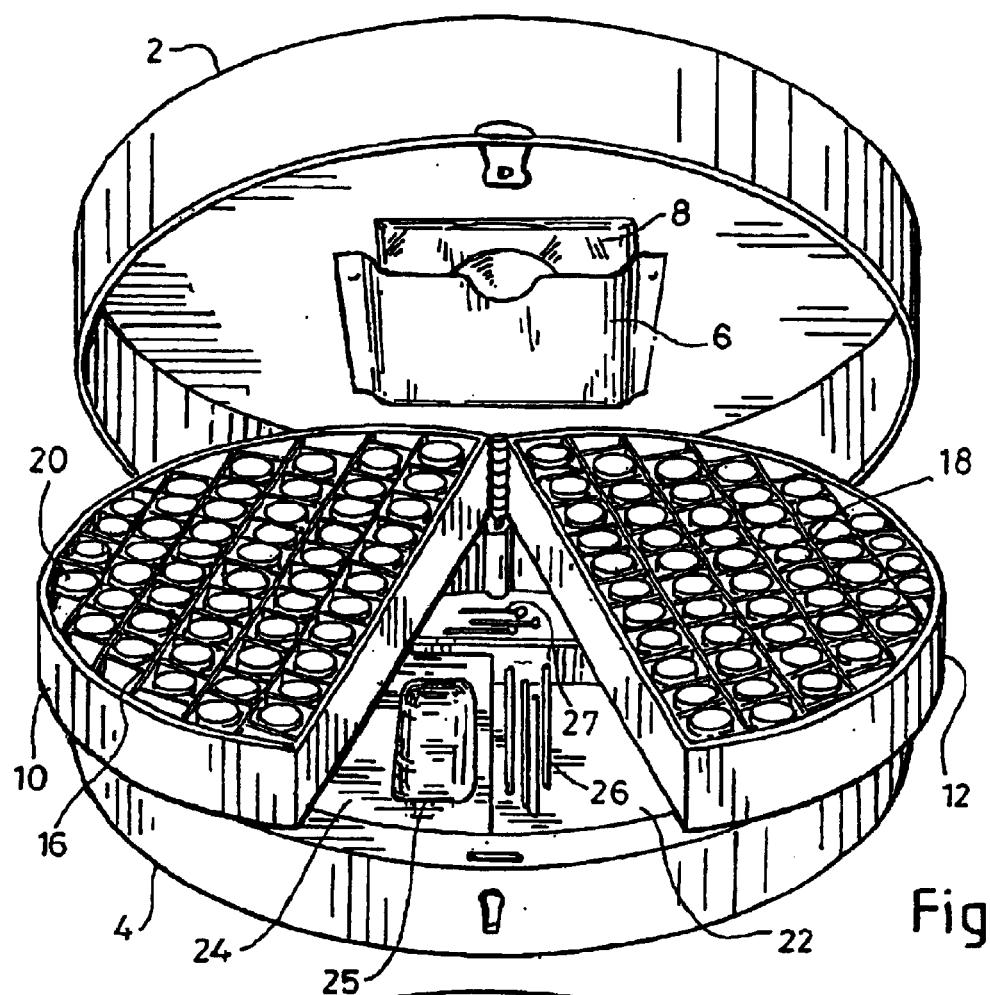
FIG. 2 shows a container (when opened) revealing various components of the apparatus, including a CD Rom.
Figure 1:
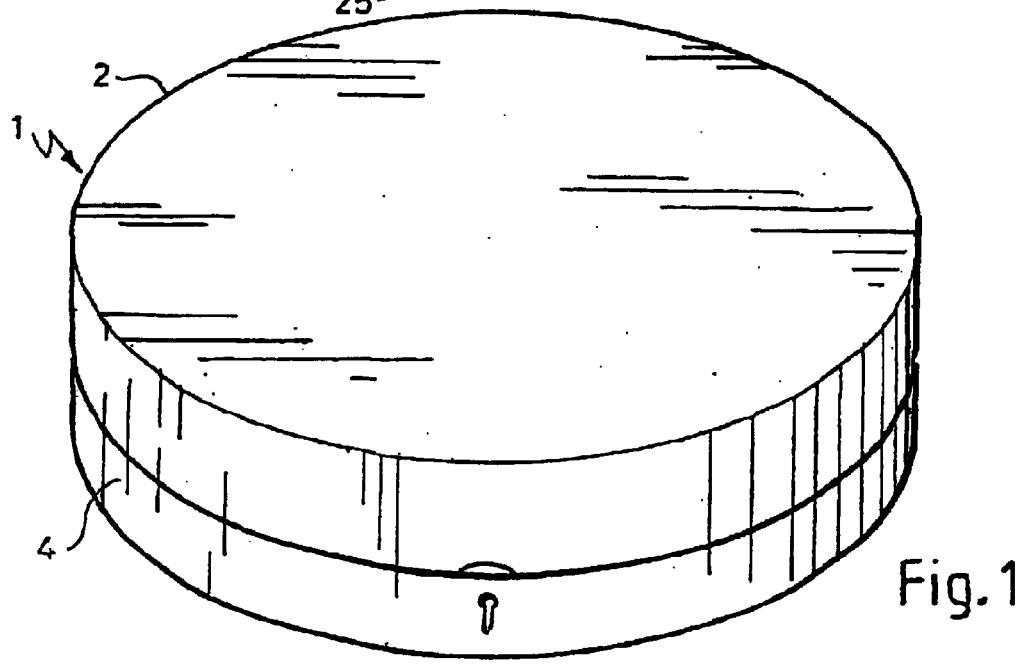
FIG. 1 shows a container for apparatus according to the invention.

With reference to FIGS. 1 and 2, apparatus in accordance with the invention comprises a container 1 which is of a generally circular shape when viewed in plan, and has a lid 2 which surmounts a base tray 4. The lid 2 and base tray 4 are pivoted together by a hinged connection at the rear of the container 1 so that the lid 2 can pivot, about a horizontal axis, from the closed position shown in FIG. 1 into the open position shown in FIG. 2. As can be seen from FIG. 2, the underside of the lid 2 carries a pocket 6 which contains a CD Rom 8.

The container also has a circular platform which sits above the tray 4 and which is composed of two semi-circular halves 10 and 12. The halves 10 and 12 are hinged together at a hinge 14 which enables them to pivot together and apart about a vertical axis at the rear of the container. The hinge 14 is mounted on guide means (not shown) which enables the hinge to slide forward as the two halves 10 and 12 are moved apart so that the separation of the two halves is not prevented by the lid 2. Each platform half provides a semi-circular tray which is divided into a number of compartments, for example 16 and 18, each which holds a respective container, for example 20, of a respective scent in liquid form. Each scent container is sealed by means of a removable lid and has markings which identify the scent within the container.

The appendix hereto is a table which lists all of the individual scents which may be contained in the platform. As can be seen from the table, the scents are divided into families, and there are a large number of individual scents which may be present. The dimensions of the described platform relative to that of the scent containers are intended to be such that the platform can hold all of the said scents. However, a simplified version of the apparatus might have a platform which holds a smaller number of scents, the minimum being one from each of the listed families.

When the platform halves are moved into the open position shown in FIG. 2, the interior of the tray 4 is revealed. This is divided into two compartments 22 and 24. The compartment 22 contains a number of paper "smelling strips" 26 (or non-paper substrates such as polymer matrices, silica or zeolites) to which the scents may be applied before being smelt. In addition, the compartment 22 contains a number of droppers (e.g. 23). The number of droppers corresponds to the number of scents so that each dropper can be used for the respective scent. In addition, there is provided a receptacle 25 into which small doses of selected scents can be supplied (using the droppers) and mixed together.

The CD Rom 8 carries a computer program for use on a personal computer. The listing of the program is not included in the present document as it can be readily prepared using standard programming techniques and the knowledge of the operations which result from running the program. In this case, the program will initially cause the computer to display a number of introductory frames, in sequence, on its display screen. Examples of these are shown in FIG. 3.

Figure 3A:
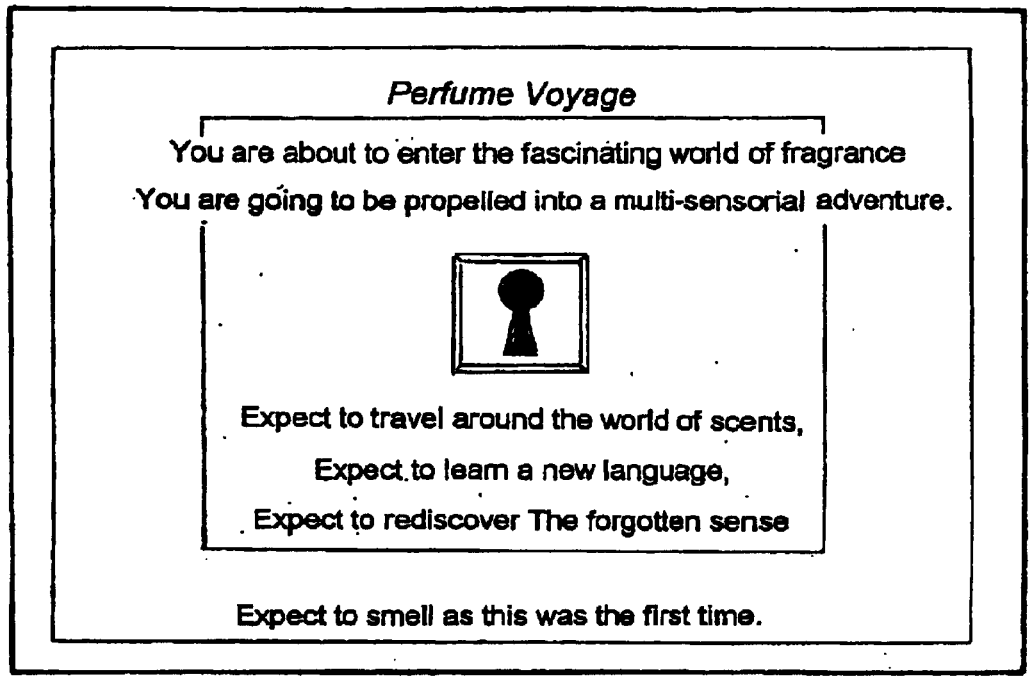
Figure 3B:
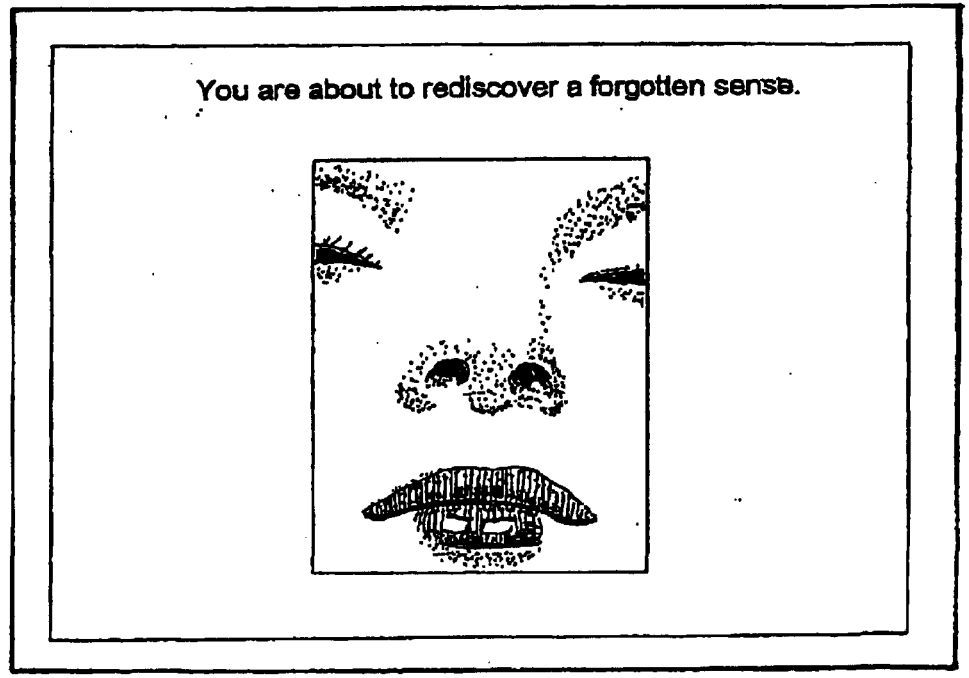
Figure 3C:
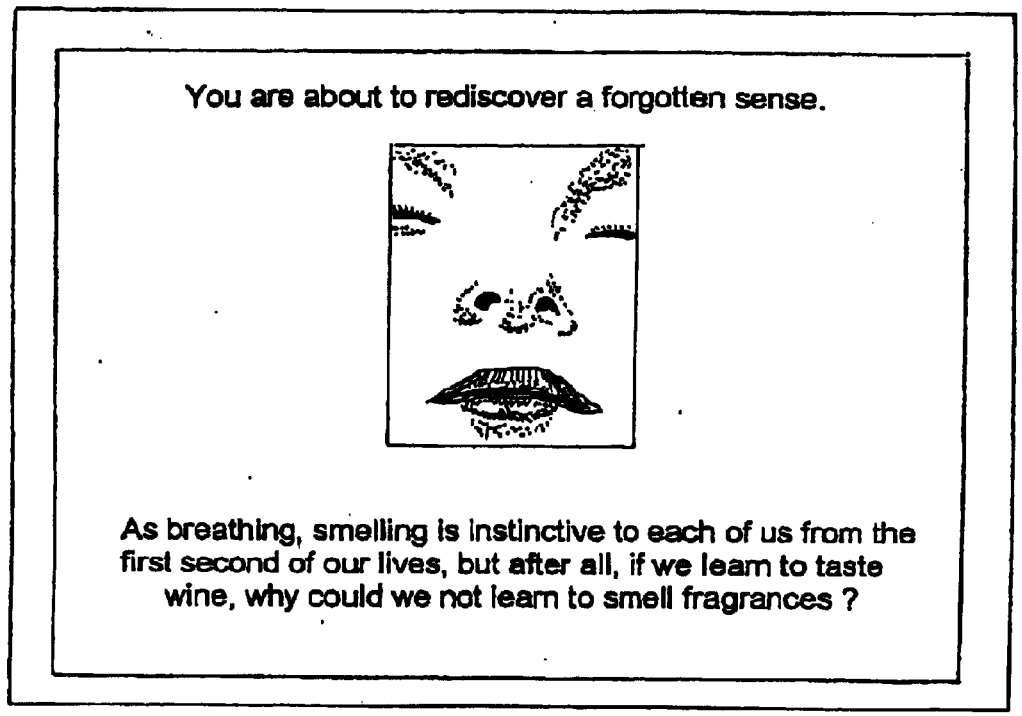
Figure 3D:
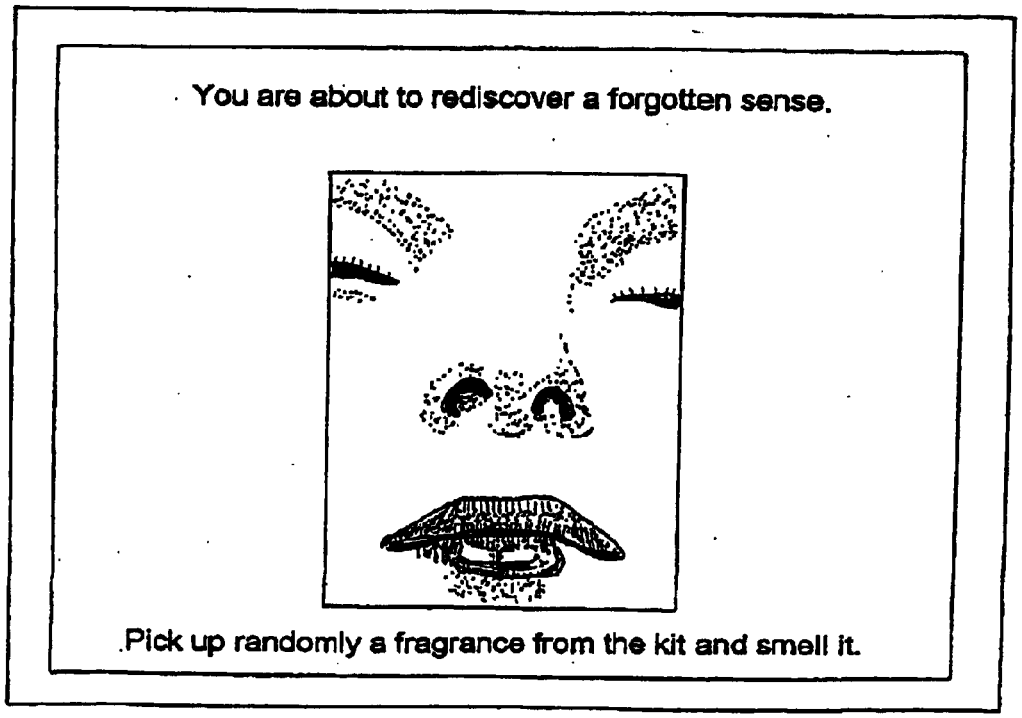
Figure 3E:
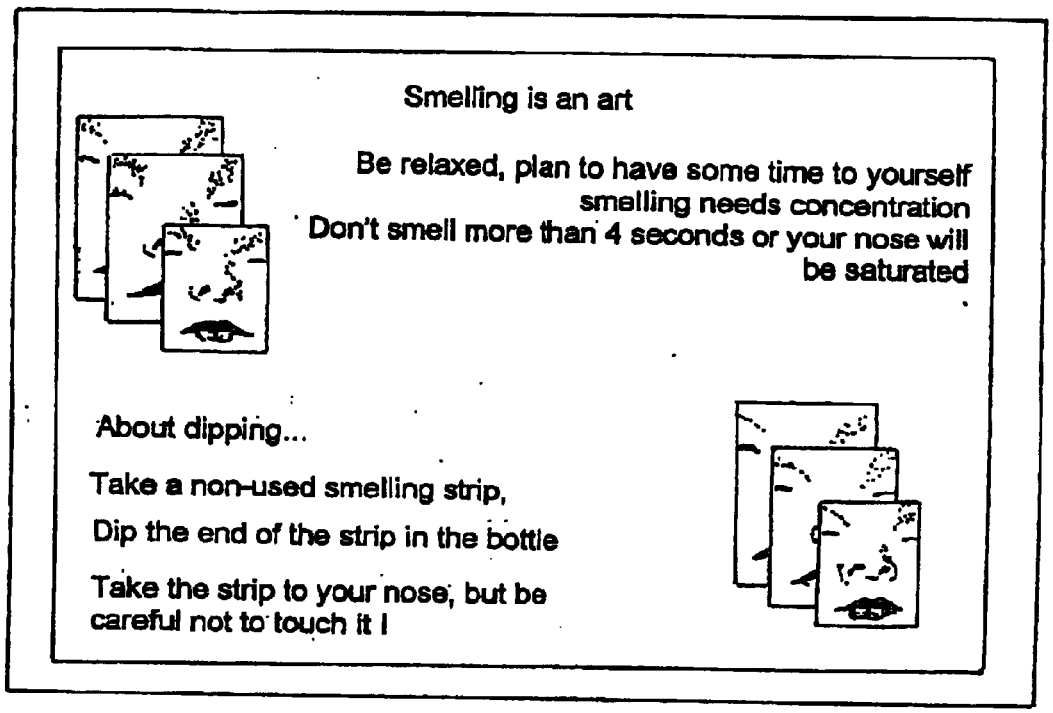

In the present example, the first frame, shown in FIG. 3A, shows a key hole against a background of containers of ingredients, and some introductory text. If the user clicks on the key hole item, this leads to the frame shown in FIG. 3B being displayed. FIG. 3B shows an image of somebody apparently appreciating a fragrance, and text which indicates that smelling, like breathing is instinctive, but that the understanding of the smells of fragrances need to be learned. This is followed by the frame of FIG. 3C, which gives further information intended to stimulate the user's interest. The frame shown in FIG. 3D prompts the user to select a scent at random and to smell it using the techniques explained in the following frame, shown in FIG. 3E.

Figure 3F:
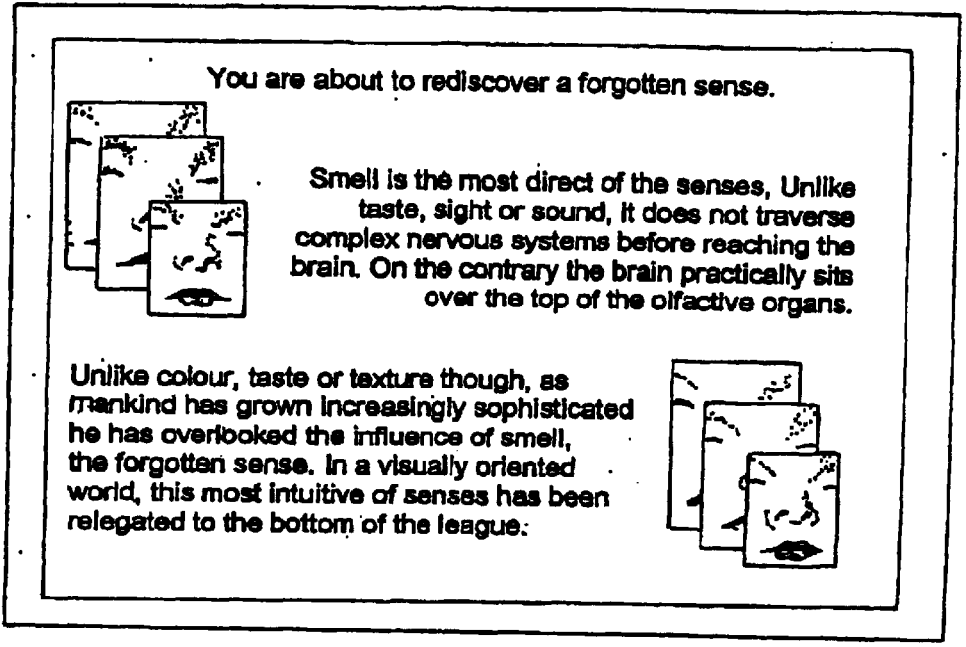
Figure 3G:
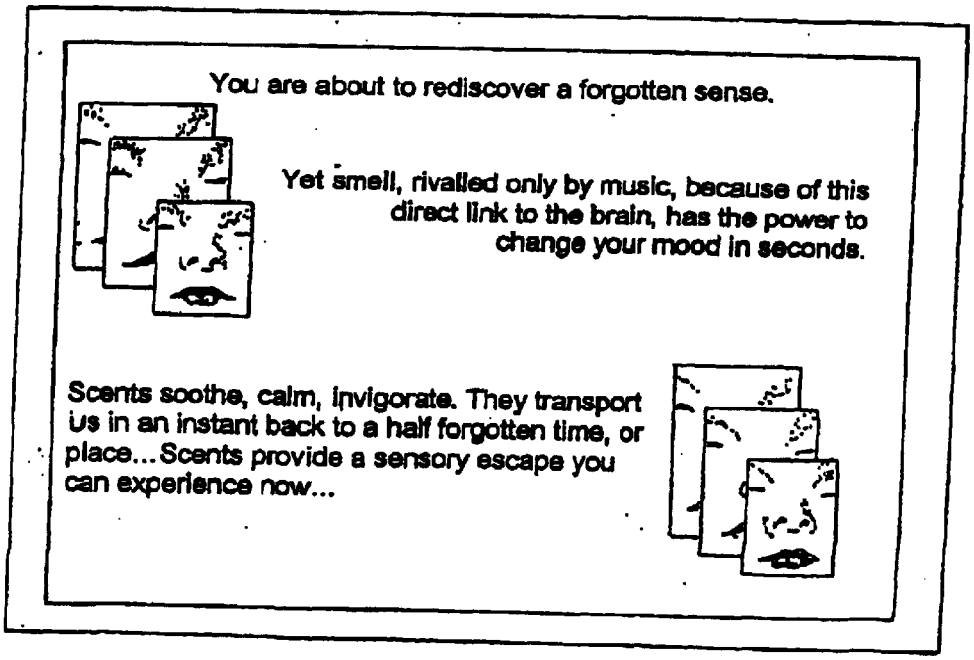

FIGS. 3F and 3G show subsequent frames which discuss the nature of smell and its potential effect on people's moods. The purpose of these frames is to stimulate the user's interest in pursuing the subsequent activity suggested by the program, and it will be appreciated that additional or alternative information may be provided at the introductory stage of the operation of the program. In addition, the program may cause the computer to display an animated figure (such as a perfumer) and play audio files so that the information in the introduction is presented in the form of a spoken narrative provided by the animated figure.

Figure 3I:
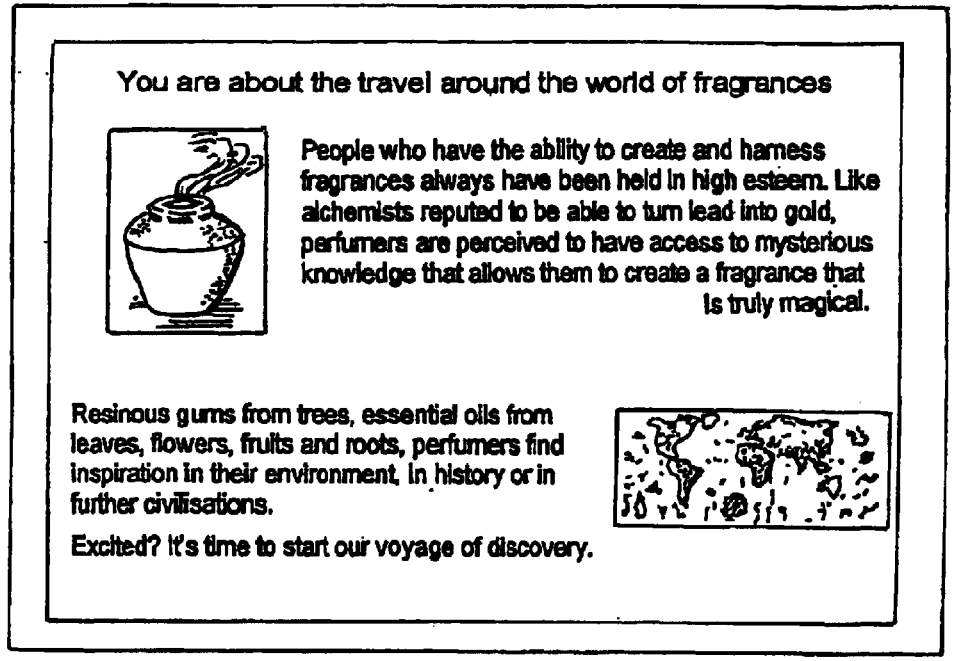
Figure 4:
FIG. 4 is a representation of a map of the world which is displayed by the computer (and stored in encoded form on the CD Rom) from which a user can select various regions, each associated with a respective scent or family of scents.

The frames shown in FIGS. 3H–I, explaining the next part of the game, are then displayed in sequence, and the program then causes the computer to display a map, one example of which is as shown in FIG. 4. Alternatively, the computer may display a globe which the user can rotate about one or more axes with the aid of a cursor.

The cursor can also be used to select a given country or region from the map. The program includes cross references between each selectable region and a respective scent or family of scents, and is so arranged that the selection of a given region will then cause the computer to display information about the cross referenced set/family.

Figure 5D:
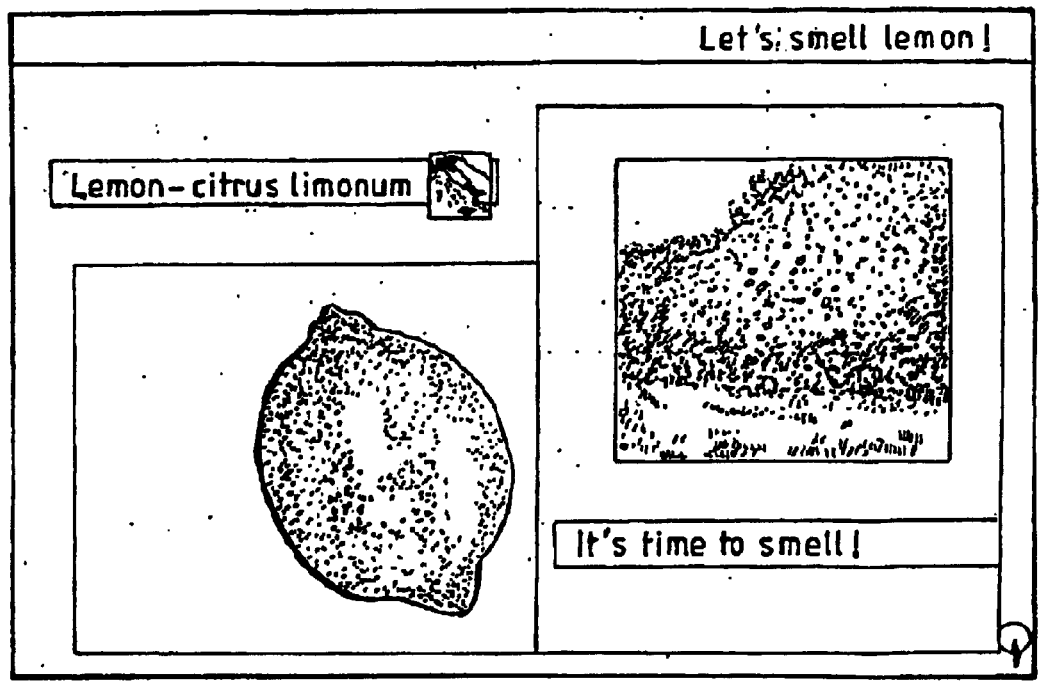
Figure 5E:
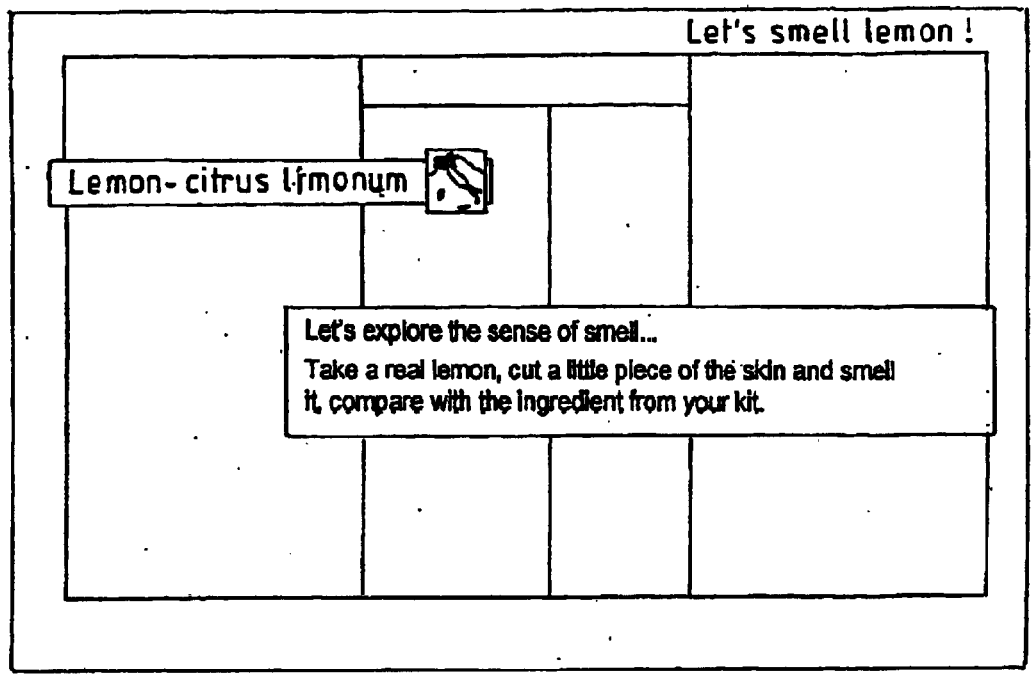
Figure 5F:
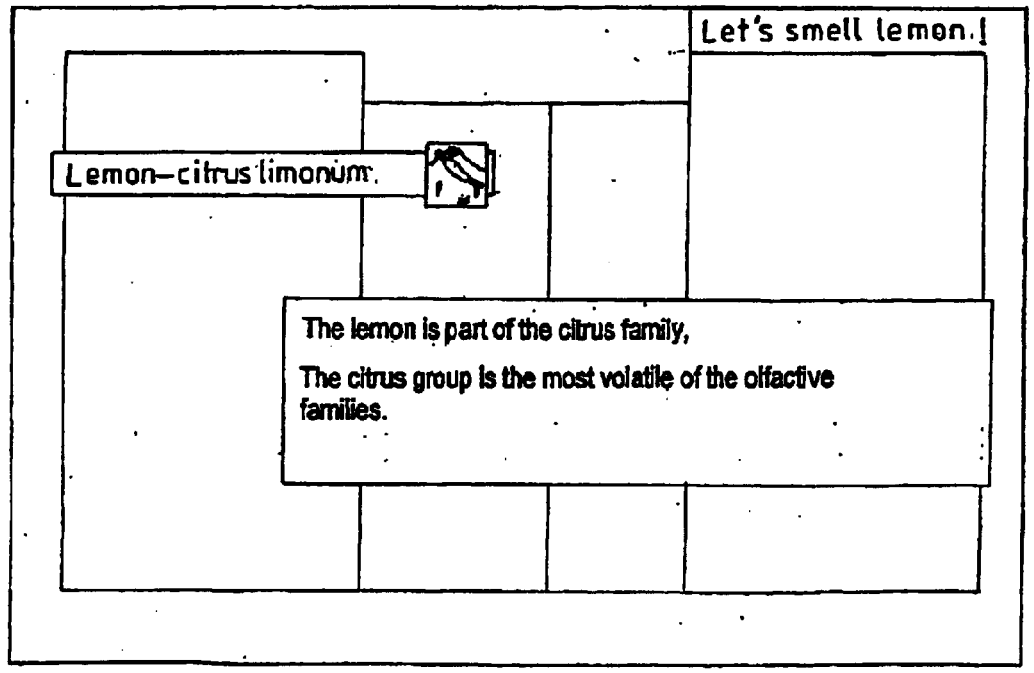

Thus, for example, the selection of Italy from the map shown in FIG. 4 will lead to the frame shown in FIGS. 5A and B being displayed. The latter frame provides a list of related scents in two olfactive families from which list, for example, lemon can be selected. The next frame, shown in FIG. 5C, gives more general information (historical, cultural, geographical etc) on lemon. This is one of the scents included in the kit, and the program therefore thus prompts the user to smell that scent (FIG. 5D). The computer program gives the user the option of inputting notes on the impressions of the scents sampled, so that the computer compiles an electronic "carnet de voyage" that the player can display on the screen whenever he/she wants. The "carnet de voyage" may also include a hypertext link to a dedicated web site for providing further information on the selected scents.

Frames 5E and 5F show further information which can be displayed about lemons These frames help to put the user in experimental situations which lead to conclusions, which are intended to lead the user to understand the advantages of using the "Lignes de Force" representation of scents discussed below. The user also learns about the olfactive family which includes lemon.

In general, a given family will be linked with several countries in the database provided on the CD Rom. Thus, for example, by clicking on another relevant country, the user can obtain data on another member of the citrus olfactive family. Thus, background data on each scent can provide information about a family which is not provided by other members of the family.

Once the player has "visited" all the ingredients, there is a recap of the fourteen families with the introduction of the "Lignes de Force" concept discussed below.

Figure 6A:
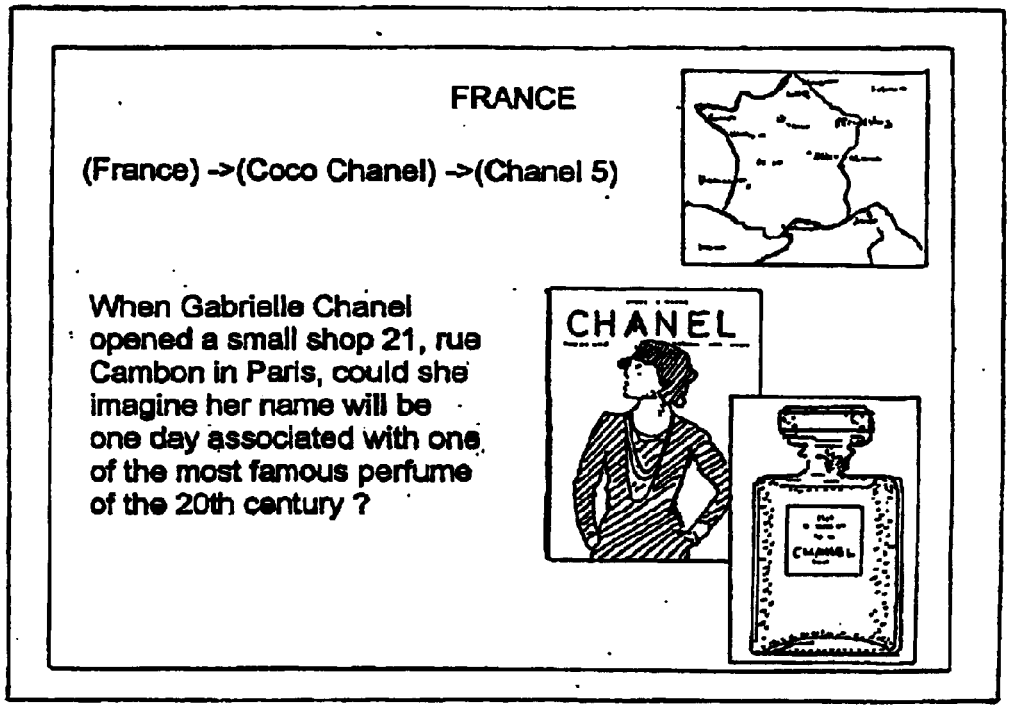
Figure 6B:
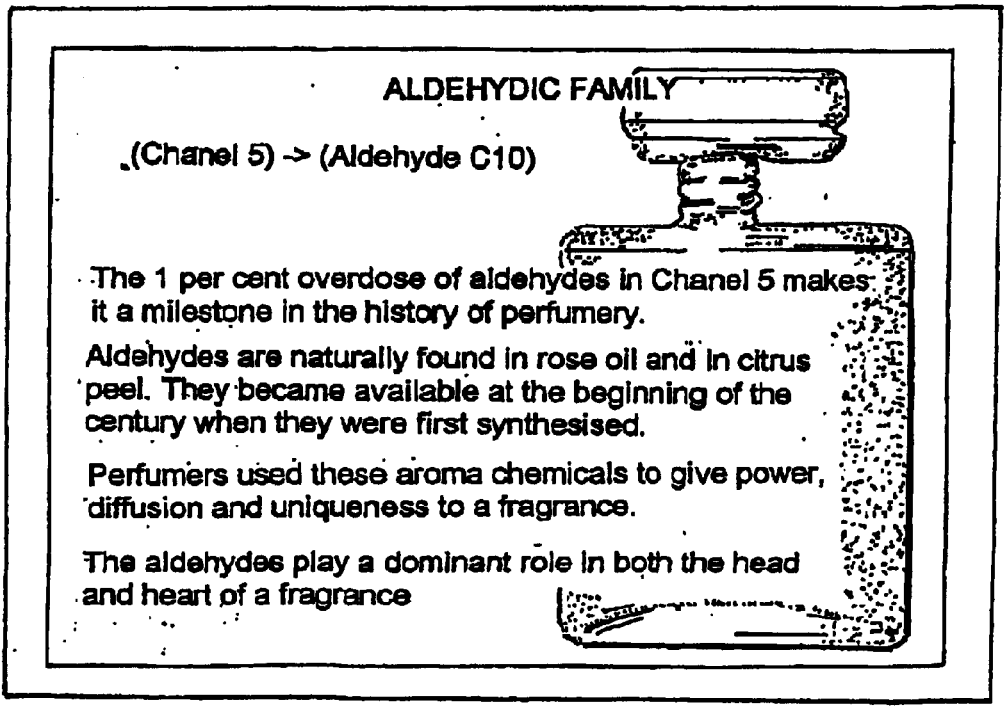
Figure 6C:
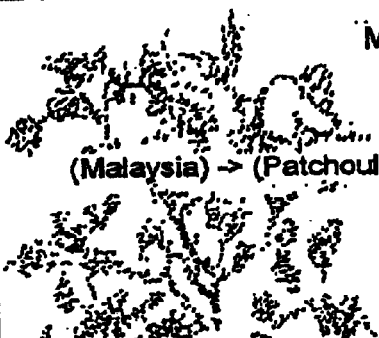
Figure 7A:
Figure 7B:
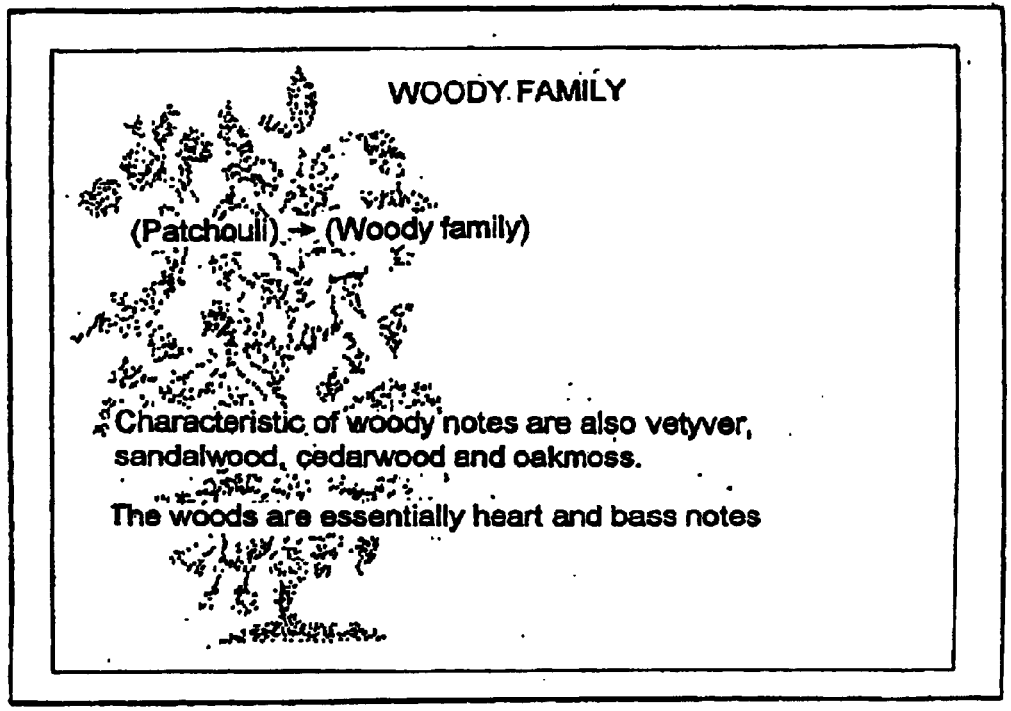
Figure 7C:
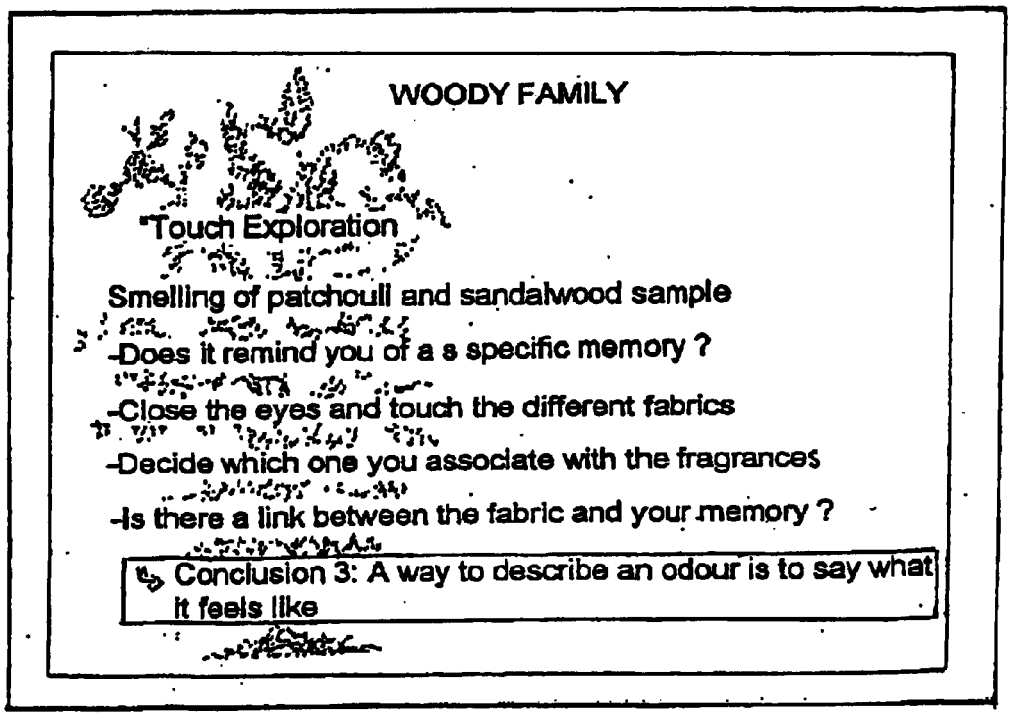
Figure 10:
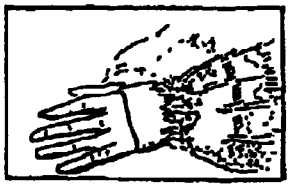
Figure 11:
Figure 14:
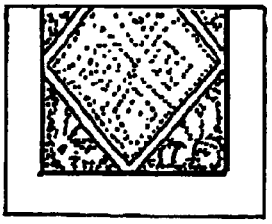
Figure 15:
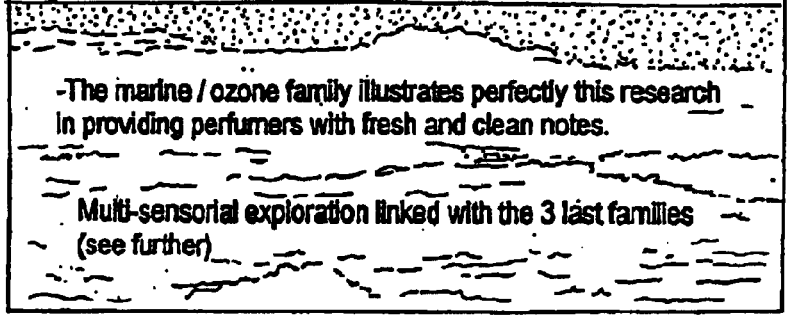
Figure 16:
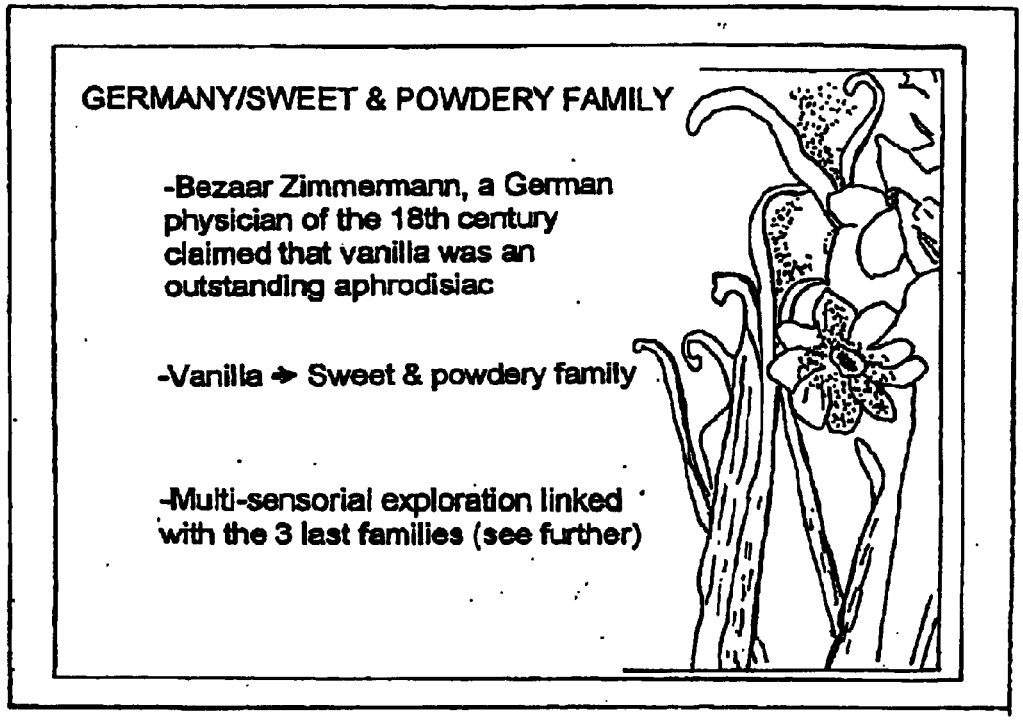
Figure 17:
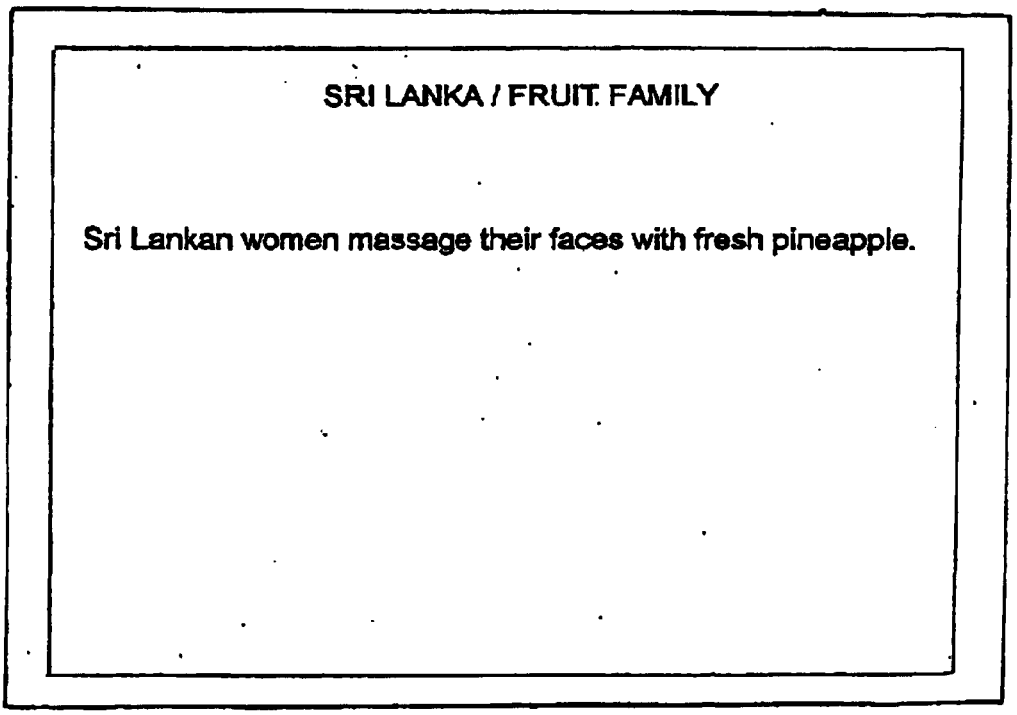

FIGS. 6A–C show the frames that would be displayed if the user were to select Paris. FIGS. 7A–C show the frames that would follow the selection of Malaysia. In each case, the first frame indicates the region (the city Paris or the country Malaysia as the case may be) and a famous scent associated therewith. The subsequent frames then provide more general information on the family of that scent. As shown on the frames, the computer can also indicate other scents (in the kit) from the same family that can be tried by the user.

FIGS. 8–17 show frames which would be displayed in response to the selection of other regions as indicated on the frames. Each of these frames prompts the user to try a sample scent from the kit. It should be noted that the kit also includes a sample of leather, and the frame shown in FIG. 13 prompts the user to smell that sample.

Once all the frames associated with any given region selection have been displayed, the map shown in FIG. 4 is once again displayed so that the user can select another region. The user can then select another region, until all of the regions have been selected and the associated frames on them displayed. At this stage of the process, the computer may display summary frames as shown, for example, in FIGS. 19 and 20.

At this stage, a further frame (not shown) is displayed prompting the user to try a representative scent from each of the families, and then to input into the computer an indication of the desirability of that scent. This indication could take the form of a score from 0 (unpleasant) to 10 (very desirable).

Figure 21A:
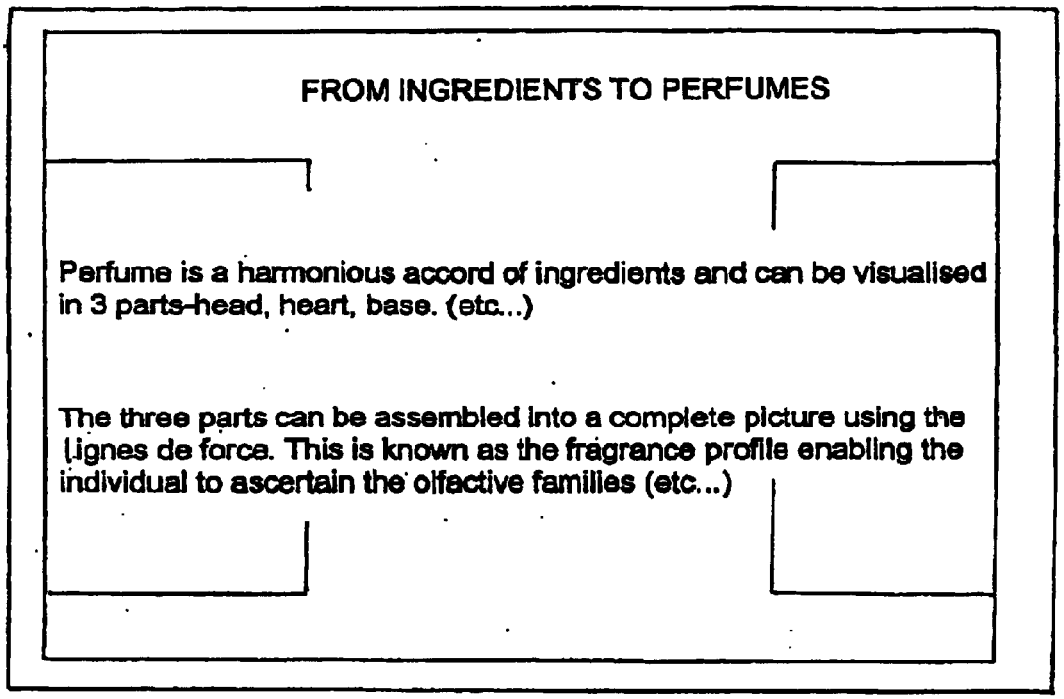
FIGS. 21A and 21B are examples of text and graphics which can be displayed to introduce the user to concepts relating to a combination of scents.
Figure 21B:
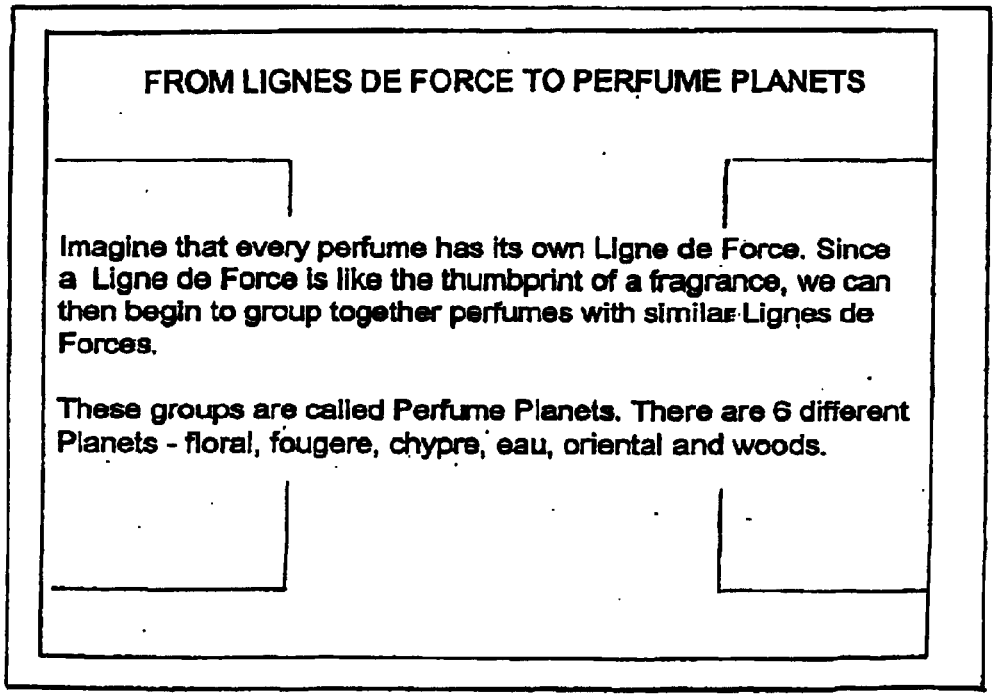

The program then provides the user with a description of the present applicants "Lignes de Force" and "Perfume Planets" method of generating symbols representative of different fragrances (starting with FIG. 21A or B). The "Lignes de Force" method This approach is already known, and will not therefore be described in detail. Briefly, a fragrance is represented as a number of families of scents as shown in the appendix. This is graphically displayed in a triangle such as triangle 28 shown in FIG. 22 The triangle 28 is divided into an upper, middle and lower portion respectively referenced 30, 32 and 34. The upper portion represents the "head notes" which are the scents that are initially prominent after application of a fragrance, but which fade within the first fifteen minutes of evaporation. The portion 32 represents the "heart notes", families of scents which are more prominent over the next three to four hours following application of the fragrance. Finally, the portion 34 is representative of the "base notes", components which are prominent during the last four to five hours of evaporation of the fragrance. The triangle 28 also contains a series of vertical lines which are colour coded to represent various families, and which are symmetrically arranged about a vertical axis of symmetry 36 so that the group to the axis 36 is a mirror image of the group of lines to the right of the axis.

The following table indicates the reference numerals used to indicate which of the vertical lines is representative of which family:

| Family | Ref. No. |
| --- | --- |
| Citrus | 50 |
| Herbal | 52 |
| Aldehyde | 54 |
| Green | 56 |
| Marine/Ozone | 58 |
| Fruit | 60 |
| Floral | 62 |
| Spice | 64 |
| Wood | 66 |
| Leather | 68 |
| Animal | 70 |
| Musk | 72 |
| Amber | 74 |
| Vanillic | 76 |

As can be seen from FIG. 22, certain families of scents, for example the vanillic family (76) are more enduring than others, for example the citrus family (50).

The triangle and scent lines shown in FIG. 22 can be considered to be a side elevational cross section of a cone which, if viewed from above, would appear as a series of concentric rings, each representative of a respective scent. This connection between the two forms is illustrated at 78 in FIG. 22 (which shows half of such a cone viewed from above).

The rings are shown more clearly in FIG. 23, again FIG. 23 corresponds to FIG. 22 in that all families are given equal prominence. In reality, however, a given fragrance will exhibit characteristics of only some of the families, and will have scents from some families which are stronger than those from others. In the current representation, this is indicated by the thickness of the rings denoting the families.

FIG. 24 is a representation of the fragrances produced by the perfume Chanel No. 5. As can be seen, the fragrance does not have any characteristics from the herbal, green, marine/ozone, fruit, leather or amber families, but does have markedly strong aldehydic, woody and floral notes.

Figure 25:
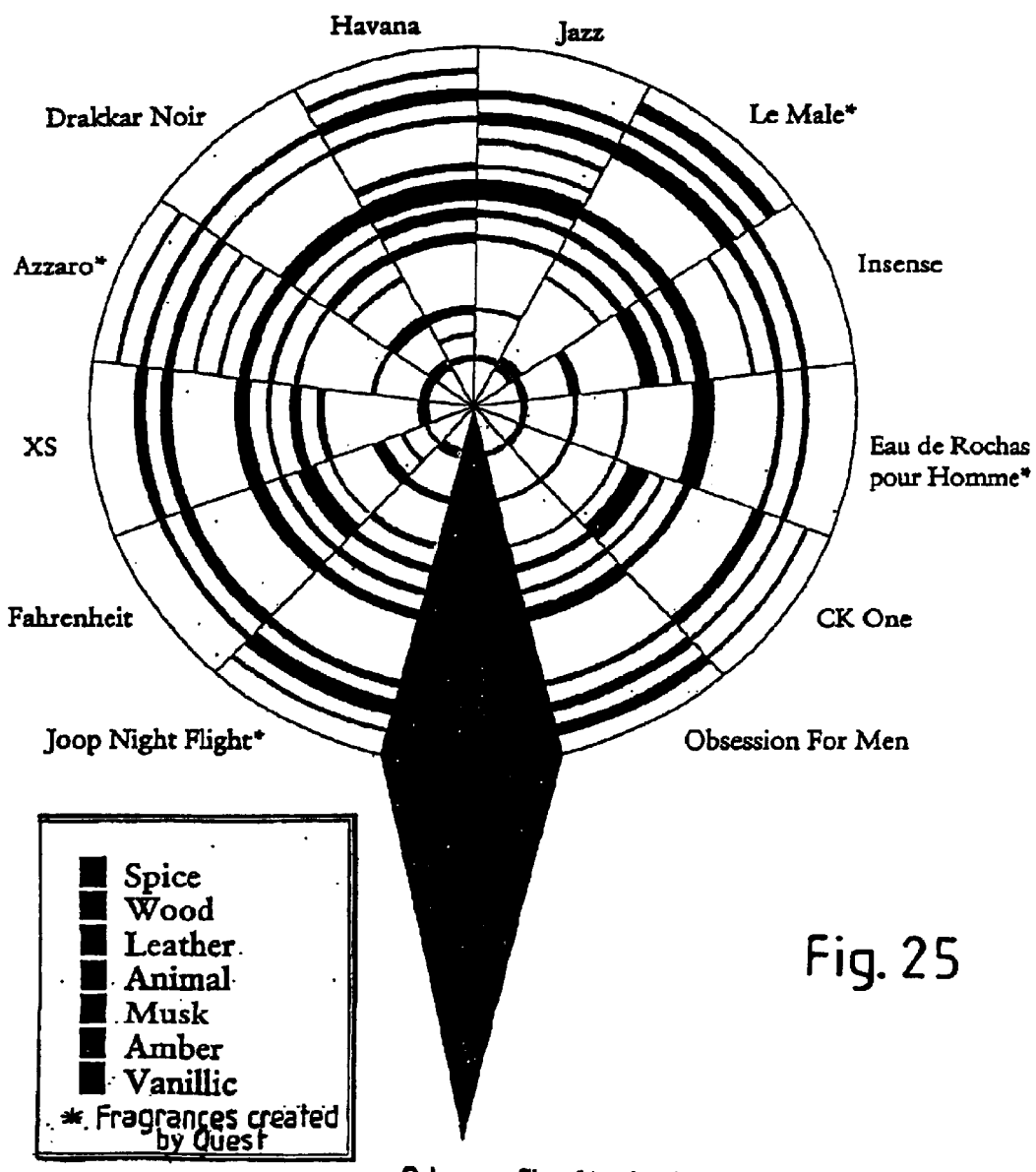
FIGS. 25 and 26 is a corresponding diagram showing the profiles of various fragrances for men and women respectively.
Figure 26:
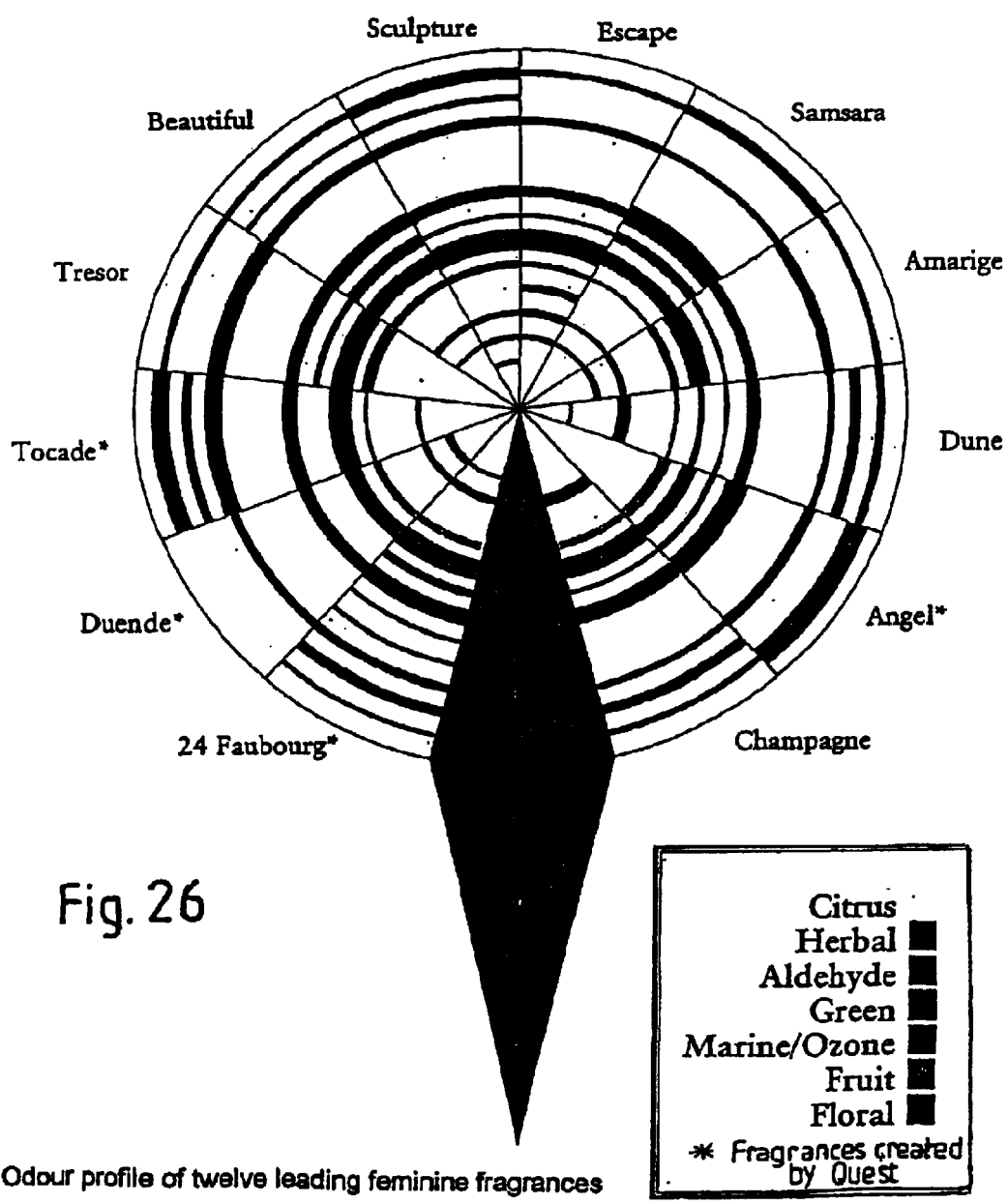

FIGS. 25 and 26 show the profiles of a number of other known fragrances. In each case, a respective fragrance is represented by a series of sectors (each one corresponding to a respective ring) which are arranged in the same sequences of rings shown in FIGS. 22 and 23, gaps indicate the absence of the scent of those families which would be represented at that radius.

Having provided these representations by way of explanation, the program will cause the computer to generate a further representation, corresponding to FIGS. 23 and 24, in which the thickness of the rings representative of families is related to the score given to each family by the user. The computer thus generates a "personalised" profile of the type of scent that the user is most likely to like, and this in conjunction with the sort of information provided on FIGS. 25 and 26 can assist the user in choosing the fragrance which he/she is most likely to enjoy.

Figure 28:
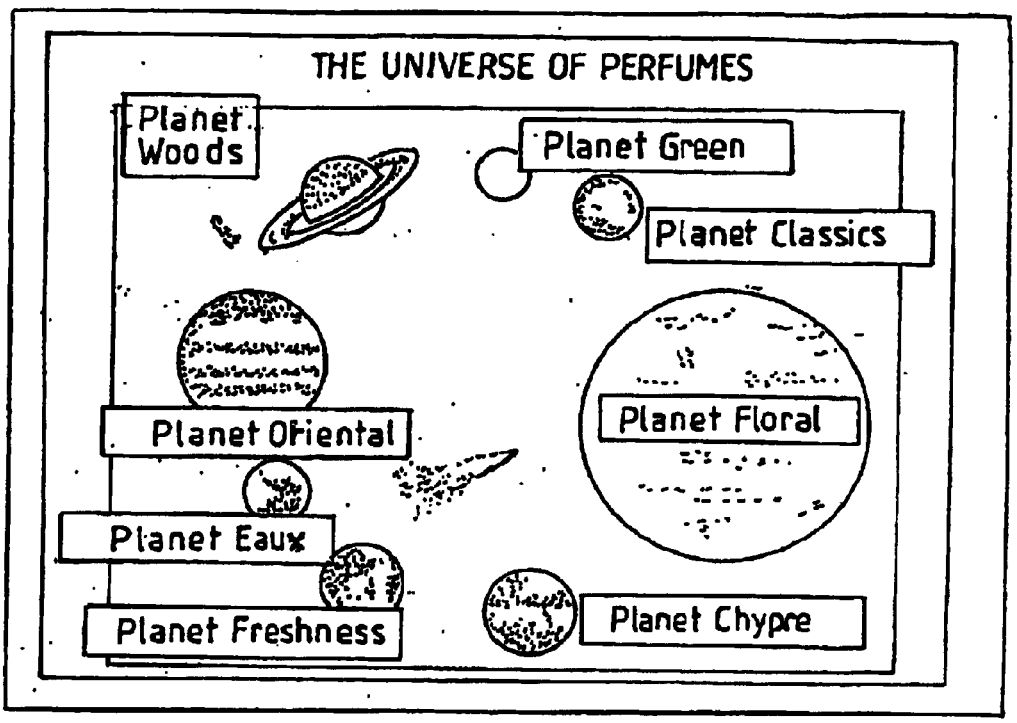
Figure 29:
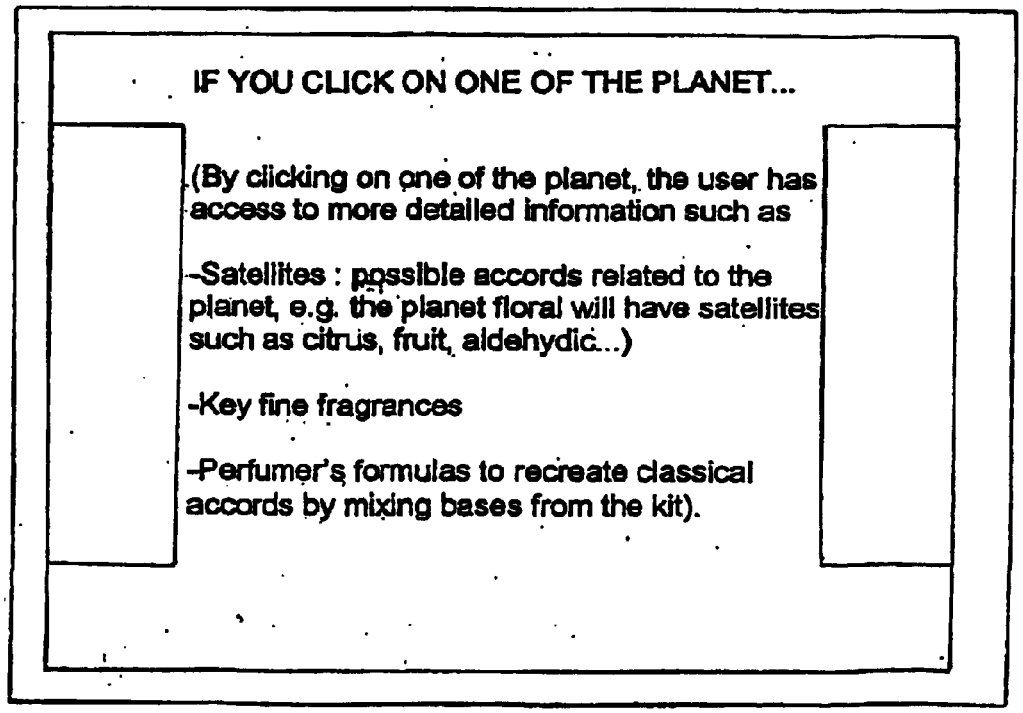

The type of scent that a person is likely to desire can be provided by asking the user a number of questions which establish a certain personality profile, and this can be used to provide further data on the types of perfume/perfume constituents that the user is likely to like. For example, the profile might suggest that the person prefers oriental scents, whereas the calculated profile suggests that floral scents are the preferred family. In that case, the computer could suggest that the user creates a perfume from an oriental base to which is added a number of floral scents. These issues are discussed briefly in the frames shown in FIGS. 27, 28 and 29. The user can use this information to create his or her own personal accords (i.e. combinations of scents).

APPENDIX

RAW MATERIALS KIT
RAW MATERIALS

| | |
|---|---|
| CITRUS | Bergamot |
| | Grapefruit |
| | Lime |
| | Mandarine |
| | Neroli |
| | Orange |
| | Petitgrain |
| | Lemon |
| | Verbena |
| HERBAL | Lavender |
| | Armoise |
| | Basil |
| | Dihydromyrcenol |
| | Oregano |
| | Peppermint |
| | Pine Needle (Acétate Iso Bornyle) |
| | Rosemary (Espagne) |
| ALDEHYDE | Aldehyde C11 |
| GREEN | Cis 3 Hexenol |
| | Galbanum |
| | Ligustral |
| | Octine Carbonate De Methyle |
| | Styralyle Acetate |
| MARINE/ | Aquantraal |
| OZONE | Calone |
| | Floral Ozone |
| | Helional |
| | Ozonal |
| FRUIT | Apple |
| | Apricot |
| | Banana |
| | Blackcurrant |
| | Coconut (Aldehyde C18) |
| | Dewberry |
| | Peach |
| | Pineapple (Heptanoate Allyle) |
| | Plum (Prunella) |
| | Raspberry |
| | Strawberry |
| | Damascone Alpha |

APPENDIX-continued
RAW MATERIALS KIT
RAW MATERIALS

| | |
|---|---|
| FLORAL | Rasberry Ketone |
| | Carnation |
| | Clover (Salicylate d'Amyl) |
| | Geranium |
| | Hedione (Methyl Dihydrojas. Su.) |
| | Jacynthe |
| | Jasmine |
| | Lilly of the Valley (Coraline) |
| | Mimosa |
| | Rose |
| | Tuberose |
| | Violet (Methyl Ionone Alpha) |
| | Ylang Ylang |
| SPICE | Bay |
| | Cardamom |
| | Coriander |
| | Cinnamon |
| | Clove |
| | Cumin |
| | Ginger |
| | Nutmeg |
| | Pepper Black |
| | Pimento Berry |
| WOOD | Cedarwood |
| | Cyclisone |
| | Cypress |
| | Iso E Super |
| | Oakmoss |
| | Orris |
| | Patchouli |
| | Sandalwood |
| | Vetyver |
| | Acetyl De Vetyveryl |
| LEATHER | Birch Tar |
| | Dynamone |
| | Isobutyl Quinoleine |
| ANIMAL | Animalis |
| | Castoreum |
| | Civet |
| | Costus |
| MUSK | Musk Ri |
| AMBER | Ambertone |
| | Cashmeran |
| | Fir Balsam |
| | Labdanum |
| | Myrrh |
| | Oppoponax |
| | Tobacco |
| VANILLIC | Benzoin |
| | Cocoa |
| | Coffee |
| | Ethyl Maltol |
| | Chocovan |
| | Coumarine |
| | Heliotropine |
| | Honey |
| | Peru Balsam |
| | Vanilla |

What is claimed is:

1. Educational/diversionary apparatus for presenting a user with scents and data thereon, the apparatus comprising a kit containing a plurality of containers holding respectively different scents and data carrying means comprising a computer readable medium which holds data on the nature, geographical origin and/or source of each of the scents, wherein data held on the computer readable medium includes a map showing a number of geographical regions and means for cross referencing each region with an associated scent, such that selection of a region by the user results in the associated scent being identified.

2. Apparatus according to claim 1, in which each scent is associated with its region by virtue of any characteristic which is relevant to that region.

3. Apparatus according to claim 1 or claim 2, in which the computer readable medium comprises a computer program having instructions for causing a computer to provide means for selecting, using an input device on the computer, an area on the map, wherein selection of any given region causes the computer to retrieve and display information on the associated scent.

4. Apparatus according to claim 3, in which the program is also operable to cause a computer running the program to invite the user to sample a scent by smelling it.

5. Apparatus according to claim 4, in which the program is also operable to cause such a computer to record data, which is entered by the user and which is indicative of his or her perception of the desirability of the sampled scent.

6. Apparatus according to claim 5, in which the program, in use, causes a computer to prompt the user to enter said data and puts the computer in a condition to receive said data after having displayed instructions for the user to try the scent and having displayed information on the scent, and before allowing another region to be selected.

7. Apparatus according to claim 6, in which the program includes instructions for causing a computer to create, from inputs, an output representative of the relative desirabilities of the previously sampled scents.

8. Apparatus according to claim 7, in which the output takes the form of a graphical representation of relative desirabilities of sample scents.

9. Apparatus according to claim 8, in which the graphical representation comprises a series of coloured elements, each corresponding to a respective olfactive group containing a scent that has been sampled.

10. Apparatus according to claim 9, in which the elements comprise concentric rings, the thickness of each of which is proportionate to the desirability of the respective scent in the group represented by that ring.

* * * * *